(12) United States Patent
Katz

(10) Patent No.: US 10,420,923 B1
(45) Date of Patent: Sep. 24, 2019

(54) METHOD AND DEVICE FOR INTRATHECAL ADMINISTERING OF IMMUNOGLOBULIN

(71) Applicant: Amiram Katz, Orange, CT (US)

(72) Inventor: Amiram Katz, Orange, CT (US)

( * ) Notice: Subject to any disclaimer, the term of this patent is extended or adjusted under 35 U.S.C. 154(b) by 209 days.

(21) Appl. No.: 15/210,076

(22) Filed: Jul. 14, 2016

Related U.S. Application Data

(63) Continuation-in-part of application No. 13/198,898, filed on Aug. 5, 2011.
(Continued)

(51) Int. Cl.
*A61M 39/02* (2006.01)
*A61M 39/04* (2006.01)
(Continued)

(52) U.S. Cl.
CPC ........ *A61M 39/04* (2013.01); *A61M 25/0097* (2013.01); *A61M 39/0208* (2013.01); *A61M 39/0247* (2013.01); *A61M 39/221* (2013.01); *C07K 16/06* (2013.01); *A61B 17/3401* (2013.01); *A61M 2039/0205* (2013.01);
(Continued)

(58) Field of Classification Search
CPC .... A61M 5/14; A61M 5/142; A61M 5/14212; A61M 5/14244; A61M 5/14276; A61M 27/006; A61M 39/0208; A61M 2039/0211–022; A61M 2039/025; A61M 2039/0276; A61M 2202/0464; A61M 2210/1003; A61M 2210/0693; A61B 17/3401; A61B 17/3472; A61K 9/0085;
(Continued)

(56) References Cited

U.S. PATENT DOCUMENTS

| | | |
|---|---|---|
| 4,543,088 A | 9/1985 | Bootman et al. ............... 604/93 |
| 4,802,885 A | 2/1989 | Weeks et al. ............ 604/288.02 |

(Continued)

OTHER PUBLICATIONS

Cada, Michaela and Johnston, Donna. Volume of Cerebrospinal Fluid Removal Prior to Intrathecal Chemotherapy Administration: A Survey of Canadian Hematology/Oncology Practitioners. Blood. vol. 118, p. 4196. Accessed Aug. 22, 2018 at http://www.bloodjournal.org/content/118/21/4196.*

(Continued)

*Primary Examiner* — Bradley J Osinski
*Assistant Examiner* — Larry R. Wilson
(74) *Attorney, Agent, or Firm* — Fattibene and Fattibene LLC; Paul A. Fattibene

(57) ABSTRACT

A device for providing an implanted injection site capable of delivering a therapeutic substance or medication into the subarachnoid space. The receiving compartment is implanted under the skin adjacent the spine. Injections may be made repeatedly into the membrane for delivering the therapeutic substance without the need for repeated spinal taps. Medications such as immunoglobulin may be administered intrathecally directly into the central nervous system bypassing the blood brain barrier providing more concentrated, effective and less costly treatment of diseases such as Alzheimer's disease. Another embodiment is a method of administering an immunoglobulin composition having a four to six percent concentration incrementally over time by alternately removing cerebrospinal fluid and injecting the immunoglobulin composition.

8 Claims, 3 Drawing Sheets

Related U.S. Application Data

(60) Provisional application No. 61/372,115, filed on Aug. 10, 2010.

(51) Int. Cl.
*C07K 16/06* (2006.01)
*A61M 25/00* (2006.01)
*A61M 39/22* (2006.01)
*A61B 17/34* (2006.01)

(52) U.S. Cl.
CPC ............ *A61M 2039/0276* (2013.01); *A61M 2210/1003* (2013.01)

(58) Field of Classification Search
CPC ........... A61K 2039/54; G01N 33/6854; G01N 33/6896
USPC ........................ 604/288.01, 288.02, 288.03
See application file for complete search history.

(56) References Cited

U.S. PATENT DOCUMENTS

| | | | |
|---|---|---|---|
| 5,326,568 A | 7/1994 | Giampapa | 424/426 |
| 5,713,858 A | 2/1998 | Heruth et al. | 604/93 |
| 6,124,437 A * | 9/2000 | Hirao | C07K 16/065 424/85.5 |
| 7,431,717 B2 | 10/2008 | Gonzales | 604/507 |
| 7,629,311 B2 | 12/2009 | Tobinick | 514/2 |
| 7,741,273 B2 | 6/2010 | McKay | 514/2 |
| 7,927,325 B2 | 4/2011 | Bright et al. | 604/523 |
| 7,963,953 B2 | 6/2011 | Kunst | 604/890.1 |
| 7,976,534 B2 | 7/2011 | Gerber et al. | 604/891.1 |
| 2002/0160933 A1 | 10/2002 | Benowitz | 514/1 |
| 2006/0009450 A1* | 1/2006 | Tobinick | A61K 31/5377 514/231.5 |
| 2006/0224102 A1 | 10/2006 | Glenn | 604/8 |
| 2010/0178289 A1* | 7/2010 | Fehlings | C07K 16/06 424/130.1 |
| 2010/0222750 A1 | 9/2010 | Cheng | 604/288.04 |
| 2011/0066111 A1 | 3/2011 | Teschner et al. | 604/187 |
| 2016/0331897 A1* | 11/2016 | Anand | A61M 5/1723 |

OTHER PUBLICATIONS

Sakka, L., Coll, G., and Chazal, J. Anatomy and physiology of cerebrospinal fluid. European Annals of Otorhinolaryngology, Head and Neck Diseases (2011) 128, 309-316. Published online Nov. 18, 2011. Accessed Aug. 22, 2018.*

Mullane et al, Drug Induced Aseptic Meningitis Caused by Intravenous Immunoglobulin Therapy, Jun. 2012, IR Med J., p. 1.

* cited by examiner

METHOD AND DEVICE FOR INTRATHECAL ADMINISTERING OF IMMUNOGLOBULIN

RELATED APPLICATION

This application is a continuation-in-part of U.S. application Ser. No. 13/198,898 filed Aug. 5, 2011 which claims the benefit of U.S. Provisional Application No. 61/372,115 filed Aug. 10, 2010, both of which are herein incorporated by reference.

FIELD OF THE INVENTION

The present invention relates in general to treating diseases, and particularly to the administering of therapeutic substances, preferably for the treatment of Alzheimer's disease, directly into the subarachnoid space and into the cerebrospinal fluid of the central nervous system.

BACKGROUND OF THE INVENTION

Treatment of neurological diseases with medications is often suboptimal due to the difficulty of medications to pass the blood brain barrier or BBB. Generally, the blood brain barrier only allows small, non-charged, or lipophilic molecules to cross. Therefore, only a minute fraction of the blood proteins are able to pass the blood brain barrier. Only about 0.01% to 0.50% of immunoglobulin G or IgG, with a molecular weight of 150 KD crosses the blood brain barrier. Accordingly, treatments with IgG targeting the central nervous system or CNS are not likely to be effective.

Generally, oral or parenteral administered medications require larger doses to achieve the desired effects than the same medications administered intrathecally. The intrathecal administration of medications may also significantly reduce side effects associated with larger oral or parenteral administered doses. Also substantial cost savings may be achieved by the significantly reduced dose required when administered intrathecally.

The customary way of accessing the cerebrospinal fluid is by performing a spinal tap or lumbar puncture. However, spinal taps generally cannot be done on a regular basis due to the associated discomfort, risk of infection, and frequent development of spinal fluid leak causing disabling headache. Medications have also been administered intrathecally, generally with an implanted pump. One such medication is baclofen used as a relaxant of skeletal muscle especially in treating spasticity. A baclofen pump is sold by Medtronic. The Medtronic baclofen pump is a programmable battery operated medical device that stores medication and is surgically placed in the abdomen and delivers the medication through a catheter inserted near the spine. These pumps are generally relatively large and cumbersome. They also generally produce a bulge from under the skin which is undesirable. The pumps are generally relatively expensive and are meant to continuously deliver non-biological materials. Additionally, the catheter use therewith is too thin for delivery of biological contents, such as proteins and cells, and the rolling pump mechanism delivering the medication has the risk of destroying the tertiary structure of proteins, which is essential to their function and could lyse cells. The pumps are generally very costly and need to be replaced every few years and require external communication with a computer system to assure proper functioning.

There have been efforts made to deliver medications with implanted devices or to the central nervous system. An implantable pump is disclosed in U.S. Pat. No. 7,927,325 entitled "Implantable Pump Connector for Catheter Attachment" issuing to Bright et al on Apr. 19, 2011. Another implanted drug delivery device is disclosed in U.S. Pat. No. 7,741,273 entitled "Drug Depot Implant Designs" issuing to McKay on Jun. 22, 2010. Another medication delivery method is disclosed in U.S. Pat. No. 7,629,311 entitled "Method to Facilitate Transmission of Large Molecules Across the Blood-Brain, Blood-Eye, and Blood-Nerve Barriers" issuing to Tobinick on Dec. 8, 2009. Therein disclosed is a method for delivering a biologic by administering parenterally into the perispinal space without direct intrathecal injection. Another device for administering a medication to the central nervous system is disclosed in U.S. Pat. No. 7,431,717 entitled "Central Nervous System Administration of Medications by Means of Pelvic Venous Catheterization and Reversal of Baton's Plexus" issuing to Gonzales on Oct. 7, 2008.

While these prior methods and devices have advanced the delivery of medications in a beneficial way they have not always delivered the medication as easily and efficiently as desired. Therefore, there is a need for a simple device that can easily provide medications to be delivered intrathecally without use of an implanted pump or repeated spinal taps.

Also, it is often difficult administering immunoglobulin therapy and complications have often arisen. Immunoglobulin therapy is commonly administered intravenously. As a result, usually relatively high doses of immunoglobulin are needed for treatment. This results in intravenous immunoglobulin therapy (IVIG) being relatively expensive. There are often adverse reactions associated with intravenous immunoglobulin (IVIG) therapy. An especially problematic and serious adverse side effect is aseptic meningitis. Aseptic meningitis is an acute inflammation of the meninges, or protective membranes covering the brain and spinal cord. As a result, it is generally believed by medical doctors in the field that intrathecal administering of immunoglobulin should not be done because of concerns about adverse reactions related to aseptic meningitis. That is, to introduce immunoglobulin intrathecally directly to the meninges in the subarachnoid space will likely increase adverse reactions including increased risk of aseptic meningitis.

Therefore there is the need for an improved method of providing immunoglobulin therapy that reduces the quantity of immunoglobulins previously administered intravenously and that is safe and effective.

SUMMARY OF THE INVENTION

The present invention permits frequent injections of a medication to be delivered intrathecally without use of a pump or having to perform repeated spinal taps. The intrathecal medication administering device comprises a receiving compartment having an injection site and a membrane that is secured under the skin and may be attached adjacent to the spine, or any other location convenient to the patient. A catheter permits medication to flow from the receiving compartment directly into a subarachnoid space for delivery of the medication to the cerebrospinal fluid of the central nervous system.

The present invention is particularly well-suited to immunoglobulin therapy that prior to the present invention has been administered intravenously. An embodiment of the present invention is a method of administering immunoglobulin therapy intrathecally. A relatively low dose or concentration of immunoglobulin intrathecally administered. The relatively low dose is less than 1.5 grams or approximately 30 mL for a 5% concentration of immunoglobulin composition. Incremental portions are administered over a period of time subsequent to removing a quantity of cerebrospinal fluid.

Accordingly, it is an object of the present invention to permit easy and repeated administering of medication to the central nervous system.

It is an advantage of the present invention that the blood brain barrier is avoided.

It is another advantage of the present invention that the administering device is adapted to be secured under the skin.

It is a feature of the present invention that a durable membrane is used that can be repeatedly punctured.

It is another feature of the present invention that a shallow curved depression provides an injection site.

It is an object of an embodiment of the present invention to provide a method of providing immunoglobulin therapy with considerably smaller doses than previously possible.

It is an advantage of an embodiment of the present invention that the cost of immunoglobulin therapy is substantially reduced.

It is a feature of an embodiment of the present invention that it is administered intrathecally over a period of time in small incremental doses.

It is yet another feature of an embodiment of the present invention that a small quantity of cerebrospinal fluid is removed prior to the intrathecal injection of the immunoglobulin composition.

These and other objects, advantages, and features will become more readily apparent in view of the following more detailed description.

BRIEF DESCRIPTION OF THE PREFERRED EMBODIMENTS

Figure 1:
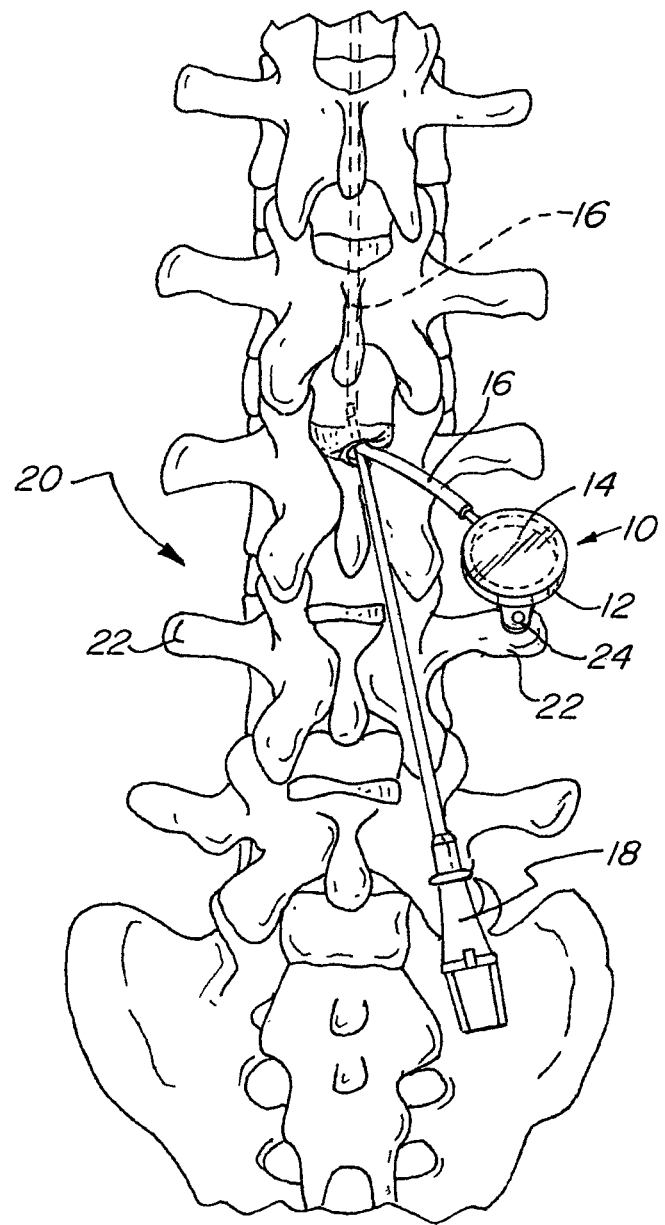
FIG. 1 schematically illustrates placement of the present invention near the spine of a patient.

FIG. 1 illustrates placement of the intrathecal medication administering device 10 under the skin adjacent the spine 20. The use of the present invention and method of introduction of a therapeutic substance or medication into the subarachnoid space with the aid of the intrathecal medication administering device 10 may be readily appreciated with reference to FIGS. 1-3. The administering device 10 comprises a receiving compartment 12 having a membrane 14 covering the receiving compartment 12. The membrane 14 is a durable membrane that can be repeatedly punctured with a hypodermic needle 30 of a syringe 32, or other delivering mechanism, containing a therapeutic substance or medication. A catheter 16 connects the receiving compartment 12 to the subarachnoid space through a lumbar puncture. The lumbar puncture and positioning of the catheter 16 is performed in a conventional way with an introducer 18. The receiving compartment 12 may be secured under the skin and attached to the transverse process 22 or in any other location convenient to the patient. The receiving compartment 12 functions as a container to administer the therapeutic substance through the catheter 16 directly into the subarachnoid space. This avoids the blood brain barrier typically encountered when therapeutic substances are administered intravenously. The therapeutic substance may be injected when needed into the receiving compartment 12 with a hypodermic needle 30 of a syringe 32 or any other delivery system and thereby introduced directly into the subarachnoid space.

Therapeutic substances that are particularly advantageous to administer with the present invention are immunoglobulins. Immunoglobulins administered intravenously (IVIG) require relatively large doses to achieve the desired concentrations across the blood brain barrier (BBB). IVIG contains the pooled immunoglobulin G (IgG) immunoglobulins from the plasma of over a thousand human donors. Intravenous immunoglobulins are widely used for the treatment of a variety of conditions including immune deficiency, idiopathic thrombocytopenic purpura, and autoimmune neurologic conditions. Despite its benefits, immunoglobulins use has been limited due to the relatively high cost. Immunoglobulins treatment usually continues for many months. Intravenous immunoglobulins treatment has shown early promise in treating Alzheimer's disease and in reducing cognitive decline. Wide spread use of intravenous immunoglobulins for the treatment of Alzheimer's disease would result in substantial shortages and expense due to the relatively large dose required for effective treatment through intravenous administering and the difficulty in producing an adequate supply.

With the present invention much smaller doses may be used effectively because the therapeutic substance or medication can be delivered more directly bypassing the blood brain barrier. This considerably reduces the cost of treatment, as well as reduces the likelihood of undesirable side effects due to the large doses of medication required when delivered intravenously. The receiving compartment 12 and catheter 16 may be sized sufficiently to permit biological, proteins and cells, to pass there through without damage or lysis.

Figure 2:
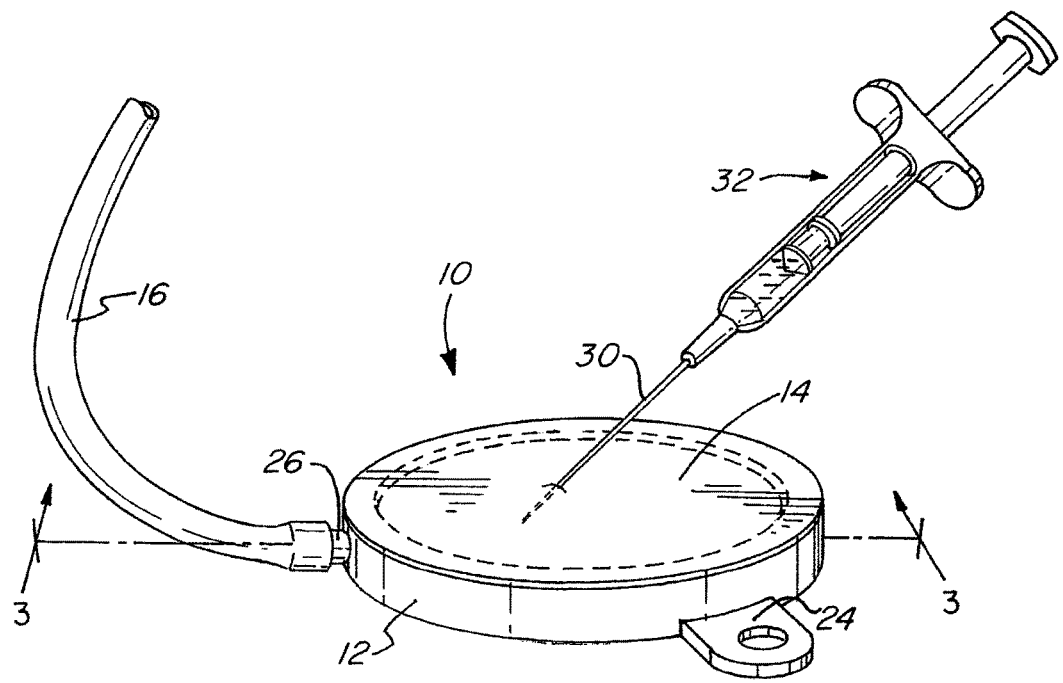
FIG. 2 schematically illustrates the administering device of the present invention.
Figure 3:
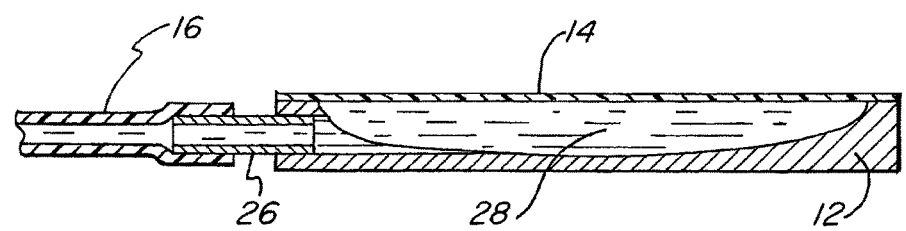
FIG. 3 schematically illustrates a cross section of the administering device illustrated in FIG. 2 taken along line 3-3.

FIGS. 2 and 3 more clearly illustrate the structure of the medication administering device 10 of the present invention. The receiving compartment 12 has a membrane 14 thereon. The membrane 14 is durable and able to accommodate multiple piercings and may be self-sealing when punctured by a hypodermic needle. An ear 24 is attached to the receiving compartment 12 and permits it to be attached to the transverse process 22 of a spine, illustrated in FIG. 1, securing its placement under the skin of a patient. A nipple 26 is connected to the catheter 16.

As best seen in FIG. 3, the receiving compartment 12 has a shallow curved depression 28. The membrane 14 and shallow curved depression 28 create a space or an injection site. This injection site is used to administer the medication directly through the catheter 16 without the need to perform a spinal tap with each injection of medication or therapeutic substance. The shallow curved depression 28 may be concave or slightly curved to facilitate the insertion of the hypodermic needle 30 through the membrane 14 and injection of the medication into the depression 28. The hypodermic needle 30 may slide on the shallow curved depression facilitating its insertion into the administering device 10. The nipple 26 is connected to the shallow depression 28 and the catheter 16 is connected to the nipple 26. However, the catheter 16 may be directly connected to the receiving compartment 12. Therefore, a therapeutic substance or medication utilized in a treatment can be injected easily and conveniently whenever there is a need without the complexity and danger of repeated spinal taps. This permits repeated or frequent treatments with therapeutic substances more directly, bypassing the blood brain barrier.

Another embodiment of the present invention is a method of providing immunoglobulin therapy. In this embodiment a method of providing immunoglobulin therapy utilizing relatively small quantities or doses of immunoglobulin that is well-tolerated by the patient has been discovered.

The method comprises performing a spinal tap on the patient by intrathecally administering the immunoglobulin therapy. An initial quantity of cerebrospinal fluid is removed from the patient. The initial quantity of cerebrospinal fluid removed is preferably between 10 and 15 milliliters or mL. An immunoglobulin composition having a concentration of between 4% and 6%, and preferably 5% of immunoglobulin is prepared. The immunoglobulin composition may be prepared with any fluid that is compatible with cerebrospinal fluid. Alternately over a period of time, preferably less than 30 minutes, a volume of cerebrospinal fluid is removed and a volume of immunoglobulin composition is intrathecally injected. The volume of cerebrospinal fluid removed is approximately one half of the immunoglobulin composition intrathecally injected. Preferably the volume of cerebrospinal fluid removed is approximately 1 mL and the volume of immunoglobulin composition intrathecally injected is preferably 2 mL. This method of alternately removing a volume of cerebrospinal fluid and injecting a volume of immunoglobulin composition results in improved tolerance and reduced unpleasantness to the patient resulting in better outcomes. The total dose of immunoglobulin composition during a single procedure should not exceed 1.5 grams or g of immunoglobulin. For a 5% immunoglobulin composition 30 mL would result in a dose of approximately 1.5 grams of immunoglobulin.

Preferably the patient is placed in a Trendelenburg position after the intrathecal injection of the total dose of immunoglobulin composition for a period of time less than fifteen minutes sufficient to allow mixing of the immunoglobulin composition with cerebrospinal fluid in the patient and then moved to a mid-Trendelenburg position for thirty minutes. The Trendelenburg position is a position with the body of the patient lying flat on their back and with their feet higher than the head and their body inclined by 15° to 30°. A reverse Trendelenburg position is where the body is tilted in the opposite direction with the head higher than the feet. A mid-Trendelenburg position, therefore, has the feet higher than the head and the body inclined between approximately 20° to 25°.

If the spinal tap is done under fluoroscopy, after injecting the immunoglobulin composition the patient's position should be switched from reverse Trendelenburg to Trendelenburg. This facilitates mixing of the immunoglobulins composition with the cerebrospinal fluid and prevents local stimulation which may lead to an unpleasant sensation for the patient.

The immunoglobulin therapy performed according to the method steps of the present invention may be repeated in different immunoglobulin therapy sessions as often as needed by the patient. The additional immunoglobulin therapy sessions may occur over the course of days or months and may continue as long as needed and effective for the patient.

Figure 4:
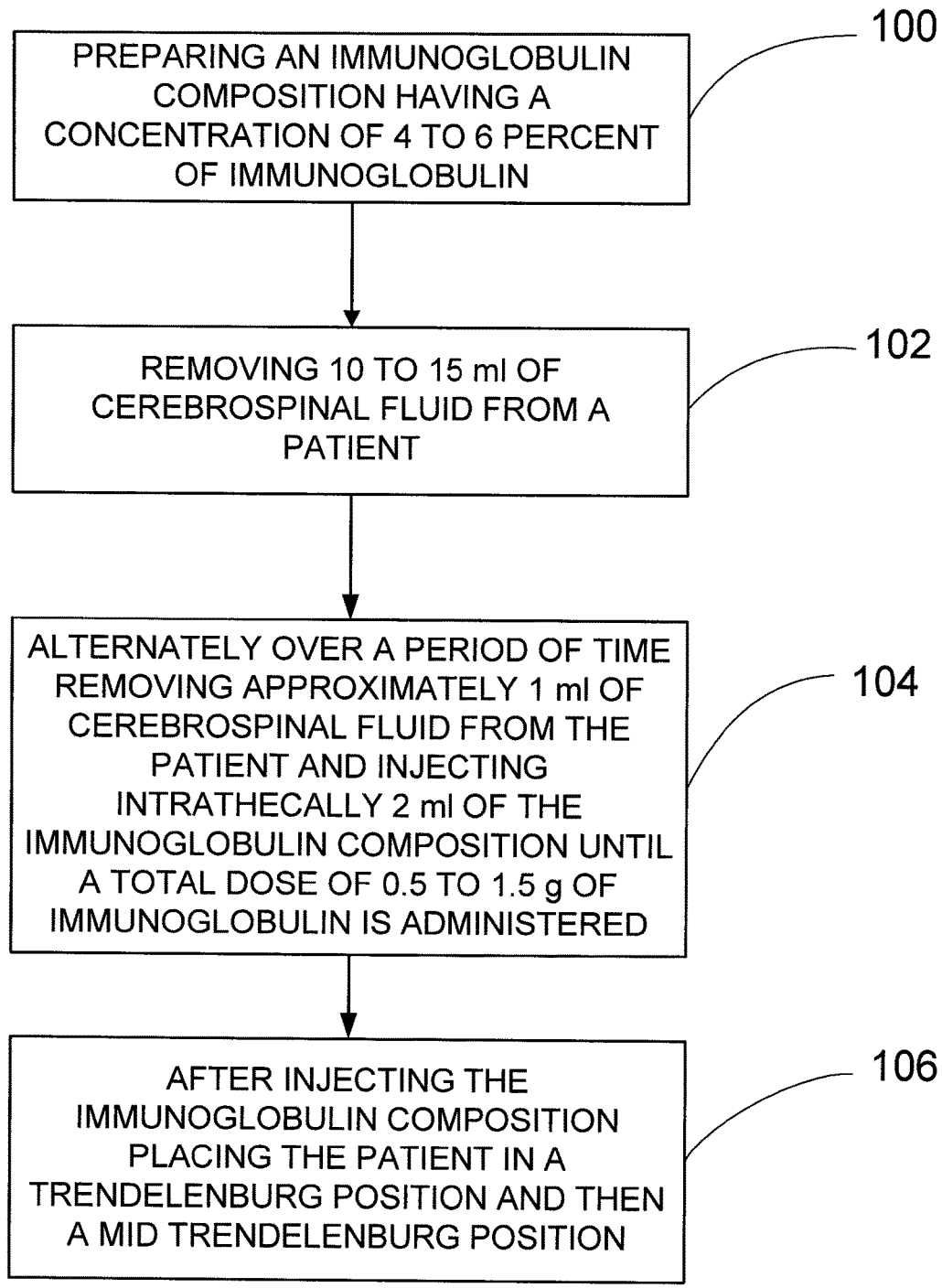
FIG. 4 is a block diagram illustrating the method steps of an embodiment of the present invention.

FIG. 4 is a block diagram illustrating the method steps of an embodiment of the present invention. Box 100 represents the step of preparing an immunoglobulin composition having a concentration of 4% to 5% of immunoglobulin. Box 102 represents the step of removing 10 to 15 mL of cerebrospinal fluid from a patient. Box 104 represents the step of alternately over a period of time removing approximately 1 mL of cerebrospinal fluid from the patient and injecting intrathecally 2 mL of the immunoglobulin composition until a total dose of 0.5 to 1.5 g of immunoglobulin is administered. Box 106 represents the step of after injecting the immunoglobulin composition placing the patient in a mid-Trendelenburg position.

This method of intrathecally administering immunoglobulin therapy has been surprisingly well tolerated by patients and has been effective in improving their condition. The method of the present invention permits effective treatment with substantially less immunoglobulin drastically reducing the cost of treatment and making the limited supply of immunoglobulin available to benefit more patients. Accordingly, the method of the present invention has the potential to improve the lives of a larger number of patients than previously possible.

The present invention makes possible widespread and cost effective treatments that could be used to help more patients than otherwise would be possible. The present invention can substantially reduce the cost of treatment and at the same time produce improved results with fewer side effects.

While the present invention has been described with respect to several different embodiments, it will be appreciated by those skilled in the art that various modifications may be made without departing from the spirit and scope of the present invention.

What is claimed is:

1. A method of treating Alzheimer's disease and delivering an immunoglobulin composition to a patient comprising the steps of:
   preparing an immunoglobulin composition having a concentration of between four to six percent of immunoglobulin as a therapeutically effective substance for treating Alzheimer's disease;
   removing an initial predetermined volume of cerebrospinal fluid from the patient; and
   alternately over a period of time removing a first volume of cerebrospinal fluid from the patient and injecting a second volume of the immunoglobulin composition intrathecally into the patient until a predetermined total dose of the immunoglobulin composition is injected intrathecally into the patient in a therapeutically effective amount for treating Alzheimer's disease,
   whereby Alzheimer's disease may be treated with immunoglobulin.

2. A method of treating Alzheimer's disease as in claim 1 further comprising the step of:
   placing the patient in a mid-Trendelenburg position after said step of alternately over a period of time removing the first volume of cerebrospinal fluid from the patient and injecting the second volume of the immunoglobulin composition intrathecally into the patient.

3. A method of treating Alzheimer's disease as in claim 1 wherein:
   the immunoglobulin composition comprises a five percent concentration of immunoglobulin.

4. A method of treating Alzheimer's disease as in claim 1 wherein:
   the initial predetermined volume of cerebrospinal fluid comprises ten to fifteen milliliters.

5. A method of treating Alzheimer's disease as in claim 1 wherein:

the predetermined total dose of immunoglobulin composition comprises less than one and one-half grams of immunoglobulin.

6. A method of treating Alzheimer's disease as in claim 1 wherein:
the first volume of cerebrospinal fluid comprises one-half the second volume of the immunoglobulin composition.

7. A method of treating Alzheimer's disease as in claim 1 wherein:
the first volume of cerebrospinal fluid comprises one milliliter and the second volume of the immunoglobulin composition comprises two milliliters.

8. A method of treating Alzheimer's disease and delivering an immunoglobulin composition to a patient using intrathecally administered immunoglobulin comprising the steps of:
preparing an immunoglobulin composition having a concentration of five percent of immunoglobulin as a therapeutically effective substance for treating Alzheimer's disease;
removing an initial volume of between ten and fifteen milliliters of cerebrospinal fluid from the patient;
alternately over a period of less than thirty minutes removing a volume of one milliliter of cerebrospinal fluid from the patient and injecting a volume of two milliliters of the immunoglobulin composition intrathecally into the patient until a total dose of thirty milliliters of the immunoglobulin composition is injected intrathecally into the patient, wherein a therapeutically effective amount of the immunoglobulin composition is injected for treating Alzheimer's disease;
after the total dose is intrathecally injected into the patient placing the patient into a Trendelenburg position for a period of time less than fifteen minutes sufficient to allow mixing of the immunoglobulin composition with cerebrospinal fluid in the patient; and
moving the patient into a mid-Trendelenburg position for thirty minutes,
whereby Alzheimer's disease may be treated with immunoglobulin and improved tolerance by the patient.

* * * * *